US00PP29316P2

(12) United States Plant Patent
Sparks

(10) Patent No.: US PP29,316 P2
(45) Date of Patent: May 29, 2018

(54) PECAN TREE NAMED 'WHIDDON'

(50) Latin Name: *Carya illinoinensis*
Varietal Denomination: Whiddon

(71) Applicant: University of Georgia Research Foundation, Inc., Athens, GA (US)

(72) Inventor: Darrell Sparks, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days. days.

(21) Appl. No.: 14/999,823

(22) Filed: Jul. 5, 2016

(51) Int. Cl.
*A01H 5/08* (2018.01)

(52) U.S. Cl.
USPC ..... Plt./153
CPC ..... *A01H 5/0825* (2013.01)

(58) Field of Classification Search
USPC ..... Plt./153
CPC ..... A01H 5/0825; A01H 5/00; A01H 5/08; A01H 5/10
See application file for complete search history.

(56) References Cited

PUBLICATIONS

2014 Fort Valley State University retrieved on Aug. 1, 2017, retrieved from the Internet at <https://portal.nifa.usda.gov/web/areera/Reports/2014/2014-Fort-Valley-State-University-and-University-of-Georgia-Combined-Research-and-Extension-Annual-Report-of-Accomplishments-and-Results.pdf> pp. 1-3.*

* cited by examiner

*Primary Examiner* — June Hwu
(74) *Attorney, Agent, or Firm* — Klarquist Sparkman, LLP

(57) ABSTRACT

A pecan tree distinguished by the following unique combination of characteristics: Consistent and acceptable fruit production, small fruit clusters, moderately early nut maturity, large nut producing mammoth kernels with excellent color and no speckling, and high resistance to scab fungus.

8 Drawing Sheets

Latin name of the genus and species of the plant: *Carya illinoinensis.*

Variety denomination: 'Whiddon'.

BACKGROUND OF THE INVENTION

The present invention relates to a new and distinct variety of pecan tree named 'Whiddon'. My new tree can be used in gardens or for commercial production of pecan nuts. This new tree was selected from seedlings grown from controlled pollination at the University of Georgia Horticulture Farm in Watkinsville, Ga., in 1990. The 'Whiddon' selection resulted from crossing 'Desirable' (unpatented) as the seed parent with 'Pawnee' (unpatented) as the pollen parent (FIG. 1). The chart of FIG. 1 illustrates the most likely pedigree of the new 'Whiddon' variety. The seedlings in the FIG. 1 chart are unnamed. All of the varieties in the FIG. 1 chart are unpatented, except for Starking Hardy Giant (U.S. Plant Pat. No. 1,361). The question marks in FIG. 1 after several of the pecan trees indicate that there is some uncertainty as to whether the identified tree is actually a part of the lineage of the new 'Whiddon' pecan tree. The resulting tree was selected when growing in a cultivated area at Watkinsville, Ga.

BRIEF SUMMARY OF THE INVENTION

'Whiddon' is distinguished from other pecan varieties known to the inventor due to the following unique combination of characteristics: consistent and acceptable fruit production, small fruit cluster, moderately early nut maturity, large nut producing mammoth kernels with excellent color and no speckling, high resistance to scab fungus (*Fusicladosporium effusum*), moderate resistance to black aphid (*Melanocallis caryaefoliae*), and moderate resistance to pecan leaf scorch mite (*Eotetranychus hicoriae*).

Asexual reproduction of 'Whiddon' by grafting, (top working) onto 'Desirable' pecan trees in 2004 and 2006 at a location in Albany, Ga. and onto 'Cape Fear' (unpatented) trees in 2006 at a location in Leary, Ga. was performed in order to evaluate these trees. Asexual reproduction of 'Whiddon' has shown that the forgoing characteristics come true to form, are firmly fixed, and are established and transmitted through succeeding propagations.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The 2001 Royal Horticultural Society (R.H.S.) Colour Chart.

BRIEF DESCRIPTION OF THE DRAWINGS

FIGS. 2-6 are of a nine year old tree.

The colors of an illustration of this type may vary with lighting and other conditions. Therefore, color characteristics of this new variety should be determined with reference to the observations described herein, rather than from these illustrations alone.

DETAILED DESCRIPTION

Botanical: The following detailed description of 'Whiddon' is based on observations of the original tree growing in Watkinsville, Ga. and of asexually reproduced progeny growing in Albany and Leary, Ga. The original tree that was approximately 26 years old at the time the application was filed and the observed progeny included nine year old 'Whiddon' trees.

Varietal name: 'Whiddon'.

Parentage:

*Seed parent*.—'Desirable'.

*Pollen parent*.—'Pawnee'.

Figure 1:
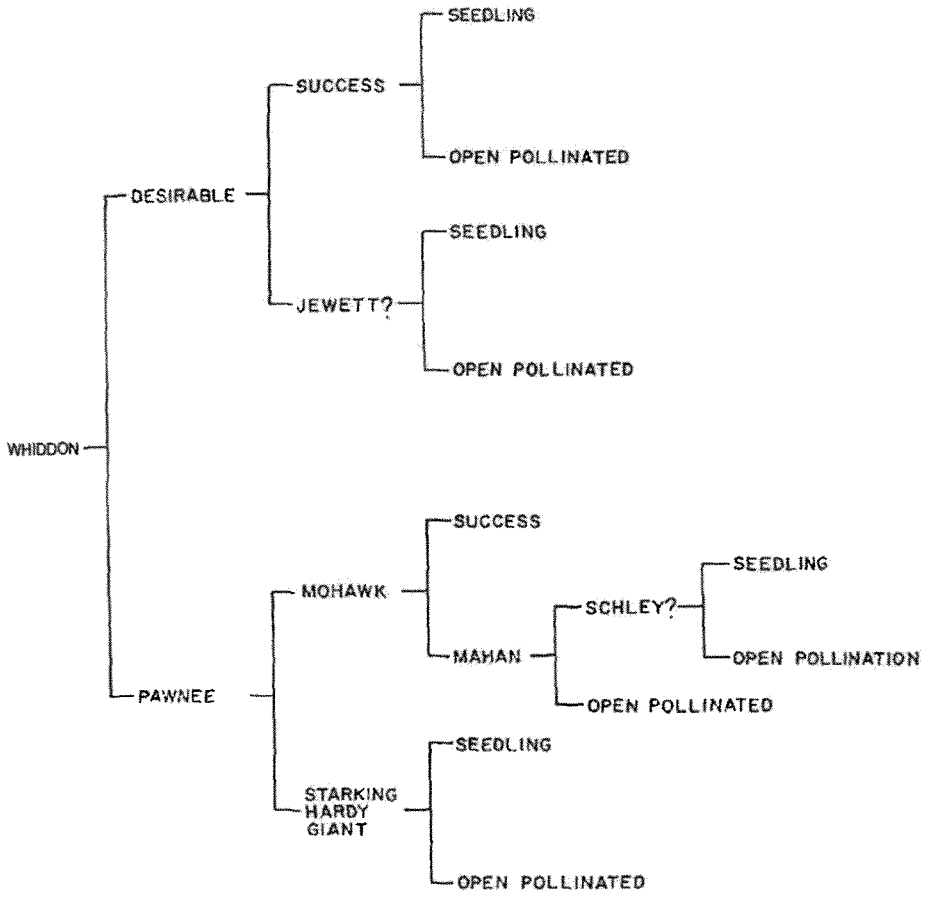
FIG. 1 is a chart showing the pedigree of 'Whiddon'.
Figure 2:
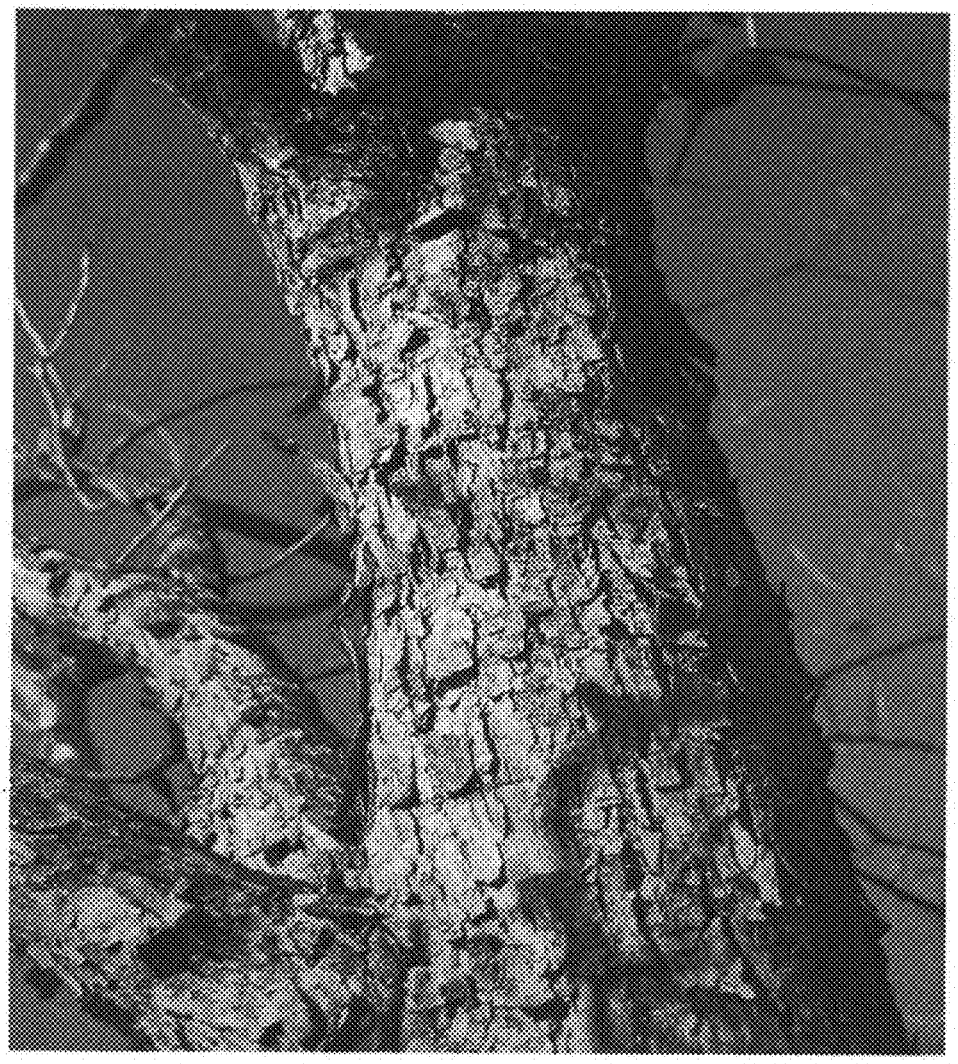
FIG. 2 is a photograph showing scaly bark of 'Whiddon'.
Figure 3:
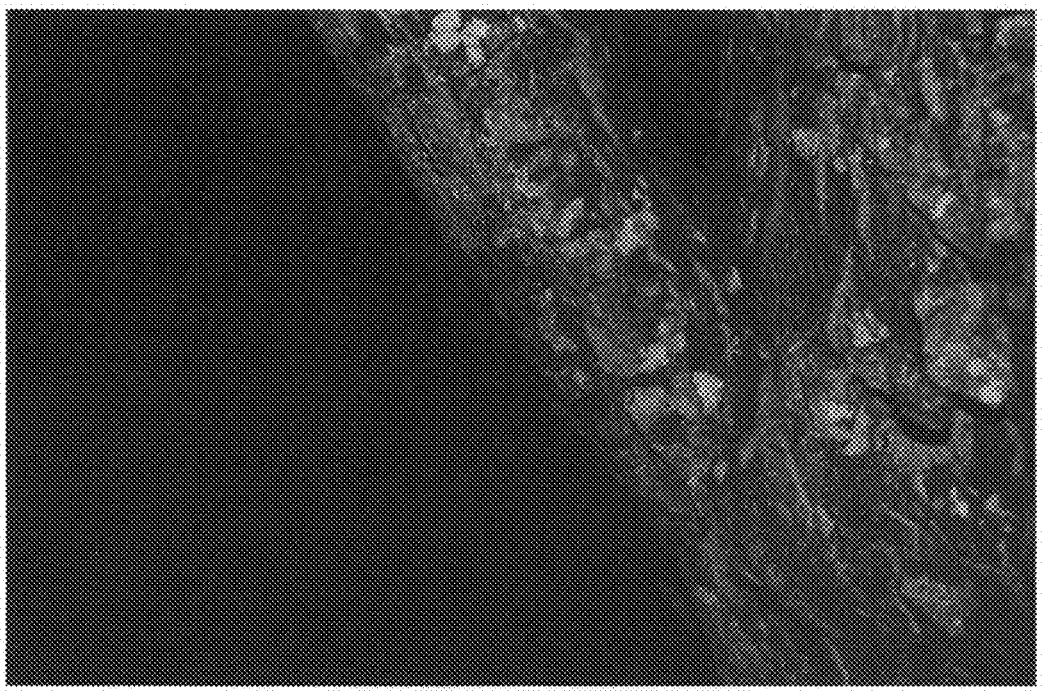
FIG. 3 is a photograph showing the narrow crotch of 'Whiddon'.

Tree:

*Overall shape*.—Upright, height to width ratio is about 2:1. FIG. 3 illustrates the characteristically narrow crotch of the upright growth habit of 'Whiddon'. Narrow crotch angles are inherent to upright tree form. Normally, narrow crotch angles split out with crop load. This is prevented in 'Whiddon' by sequential interlocking of cambium growth of the branch and the trunk. Note the incipient interlocking (debarked reddish area) at the junction of the branch and trunk in FIG. 3.

*Vigor*.—Vigorous, prolific, 'Whiddon' fruited the second year after grafting (top working) onto 'Desirable' trees and has done so in subsequent years. Original tree fruited 13 years from seed.

*Height*.—Of original tree, about 32 meters.

*Width*.—Of original tree. About 16 meters.

*Trunk*.—Of original tree (measured ½ meter above ground level) about 0.4 m diameter.

*Trunk bark texture*.—Initially, the bark is tight, but the bark becomes scaly with tree maturity. Trunk bark color: Grey (RHS 202B).

*Patches*.—Mature trunk bark characteristically has holes pecked by yellow bellied sapsucker (*Sphyrapicus varius*).

*Branch color*.—Branch shoots in woody stage are Grey-brown (RHS 199A) in color with Grey-brown lenticels (RHS 199D) that are elongated and about 1 mm long by 0.05 mm wide.

*Internodes*.—Average length is about 2.0 cm, $3^{rd}$ and $4^{th}$ leaf from base of shoot.

*Disease and insect resistance*.—Very high resistance to scab disease. [*Fusicladosporium effusum* (G. Winters) Partridge & Morgan-Jones]. Moderate resistance to both black aphid *Melanocallis caryaefoliae* (Davis) and pecan leaf scorch mite *Eotetranychus hicoriae* (McGregor).

Figure 4:
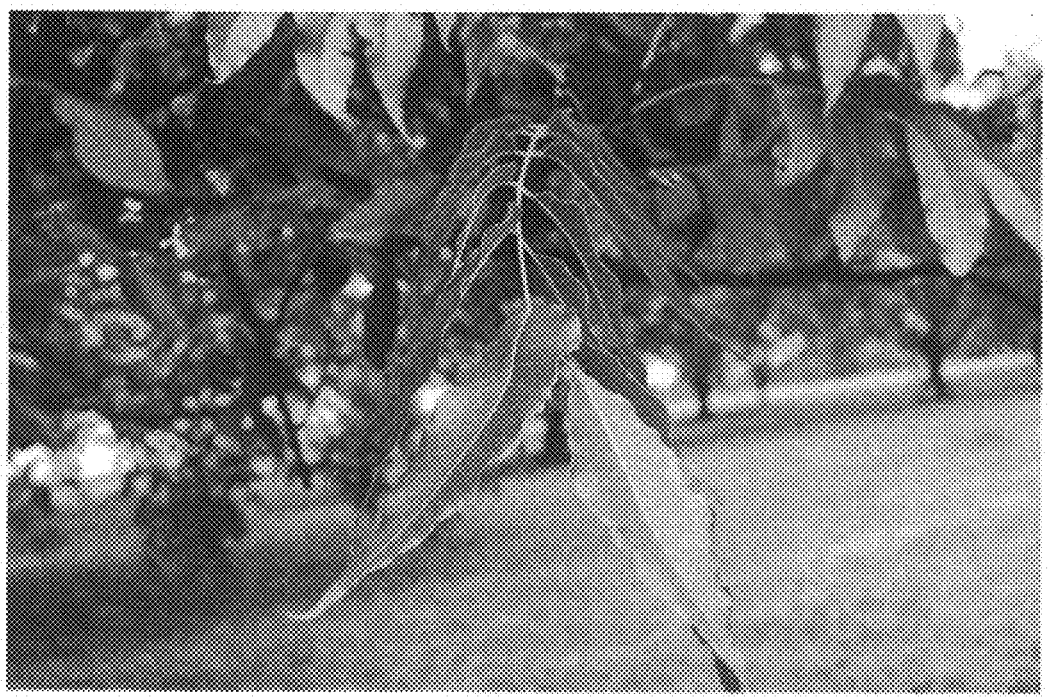
FIG. 4 is a photograph of leaf architecture of 'Whiddon'.

*Leaves*.—The mature leaf is odd pinnate compound, deciduous with leaflets having a forest green color (RHS 137A). Thirteen to 15 leaves per shoot with 11 to 17 leaflets per mature leaf. FIG. 4 illustrates the leaf architecture of the 'Whiddon' pecan. Leaflets droop non-curving from the rachis at about 45 degrees creating a narrow "tunnel" configuration. Leaflets' acropetal margin flare upward producing a subtle ruffed appearance. Leaflet blade is convoluted. Size of mature leaf (fourth leaf from base of shoot): 31 cm long, 21.6 cm wide.

*Peduncle*.—Round in cross-section, tan in color (RHS 199B). The length of the peduncle of the fourth leaf from the base is about 5.6 cm. The diameter of the peduncle of the fourth leaf from the base is about 2.5 mm.

*Leaflet*.—Size and shape: Fourth leaflet on fourth leaf from base, is 15.8 cm long by 3.6 cm wide. Falcate in shape. Base oblique. Leaflet margins are non-convoluted on mature trees but on young vigorous trees convolution increases from basal to apical leaves on the shoot. Texture: Upper leaflet surface smooth. Sheen: Upper leaflet surface glossy. Petiole: Sessile or nearly so. Margin: Serrate. Tip shape: Acuminate and narrow. Leaflet color: Upper leaf surface: Dark green (RHS 139A). Lower leaf surface: Green (RHS 138A). Pubescence: Upper leaf surface is not pubescent. Lower leaf surface is slightly pubescent.

Inflorescence:

*General*.—The 'Whiddon' pecan is monoecious, anemophilous, and protandrous (Table 1).

*Flowers*.—Pistil flowers are borne on a determinate spike, with staminate flowers borne on a determinate pendulous catkin. Two-five individual pistillate flowers per spike, borne alternately on terminally-positioned spikes. The pistillate flower is symmetrical with no stamens or petals. The pedicels are sessile. The staminate or catkin length is 77 mm and width is 4.9 mm. The staminate color is green (RHS 144B) with gold pollen (RHS 3A). The involucre size, includes the stigma, is 5.9 mm long and 2.1 mm wide. Anthocyanin is strong. The flower has one pistil with an oxblood red (RHS 61A) stigma. The flower has four bracts, which are green (RHS 144A), lanceolate, 5.1 mm long by 1.1 mm wide and are fused at the bases, forming a copular involucre.

Fruit: Mature fruit is dehiscent.

Figure 5:
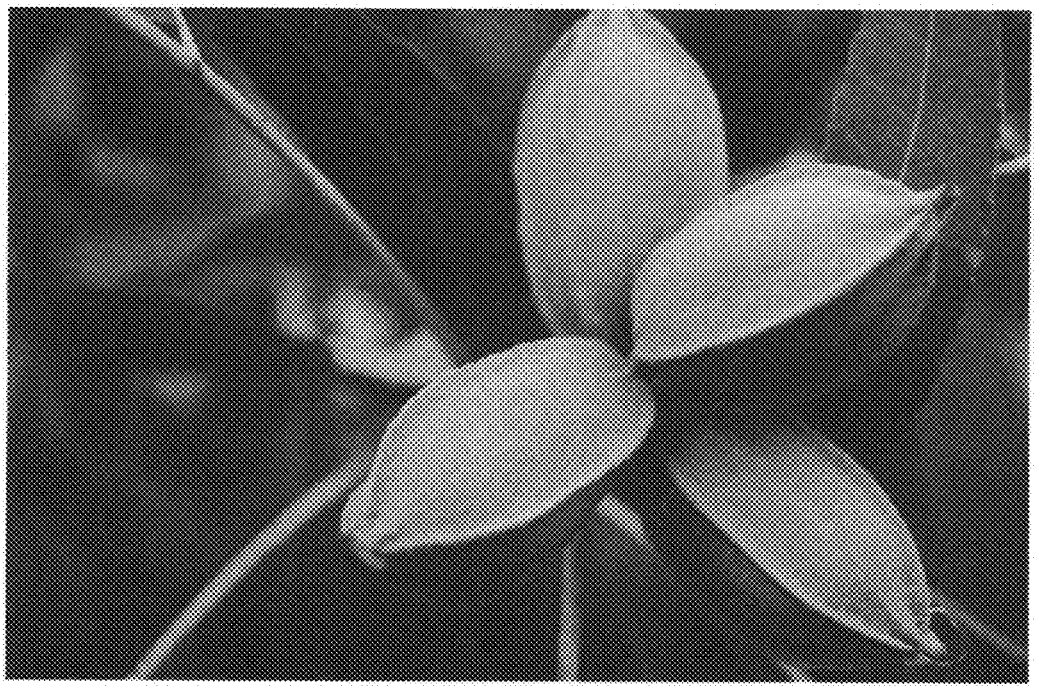
FIG. 5 is a photograph of young fruit of 'Whiddon'.
Figure 6:
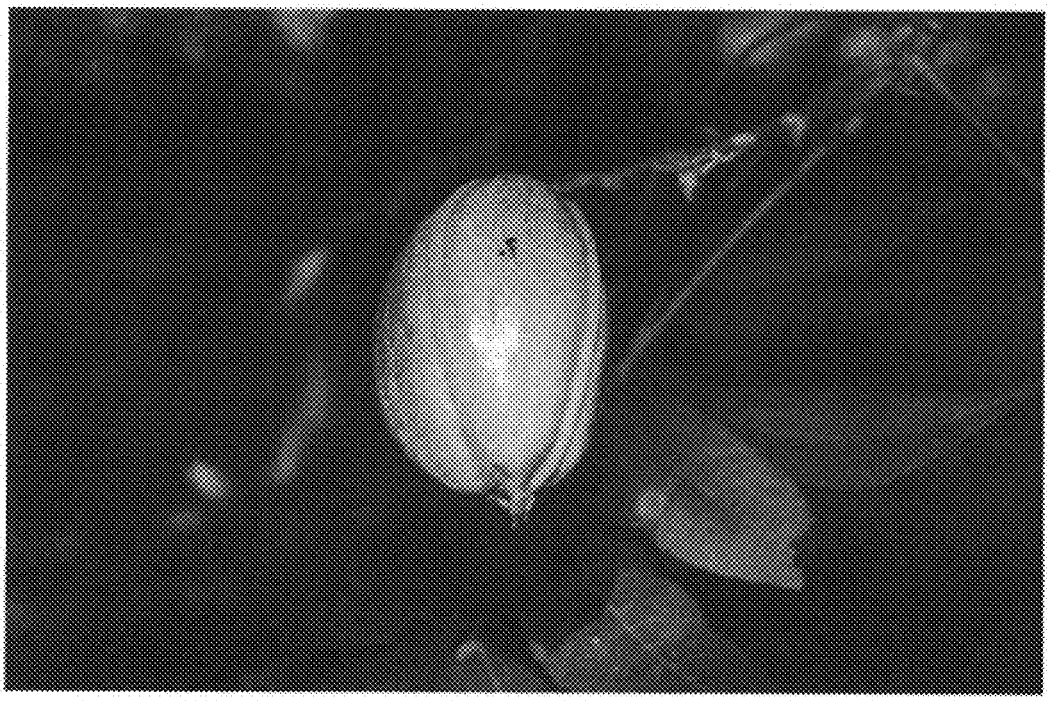
FIG. 6 is a photograph of a mature fruit of 'Whiddon'.

*Shuck*.—Green (RHS 144B) but slightly stippled near maturity. Open widely during dehiscence. FIG. 5 illustrates the fruit of 'Whiddon' at about seventy days before nut maturity. The shuck sutures are slightly winged and prominent and the apex is tapered. FIG. 6 illustrates the fruit of 'Whiddon' just prior to shuck dehiscence. The shuck surface is slightly stippled. The suture is not serrated.

*Fruit split during water stage*.—Not observed to be a problem.

*Shuck decline*.—Shuck dieback during kernel formation has not been observed to be a problem.

Nuts: (Observations from a limited number of typical nuts from several growing seasons in Watkinsville, Ga.).

*Size*.—Large, length about 45 mm, width about 25 mm (width measurement taken midway along the length of the nut and across sutures); length to width ratio about 1.8. Nut flatness (ratio of width across sutures to width between sutures) is about 1.0.

*Form*.—Oblong with a round cross-section, base shape round apex slightly cuspidate-cuspidate asymmetric with a grooved apex.

Figure 7:
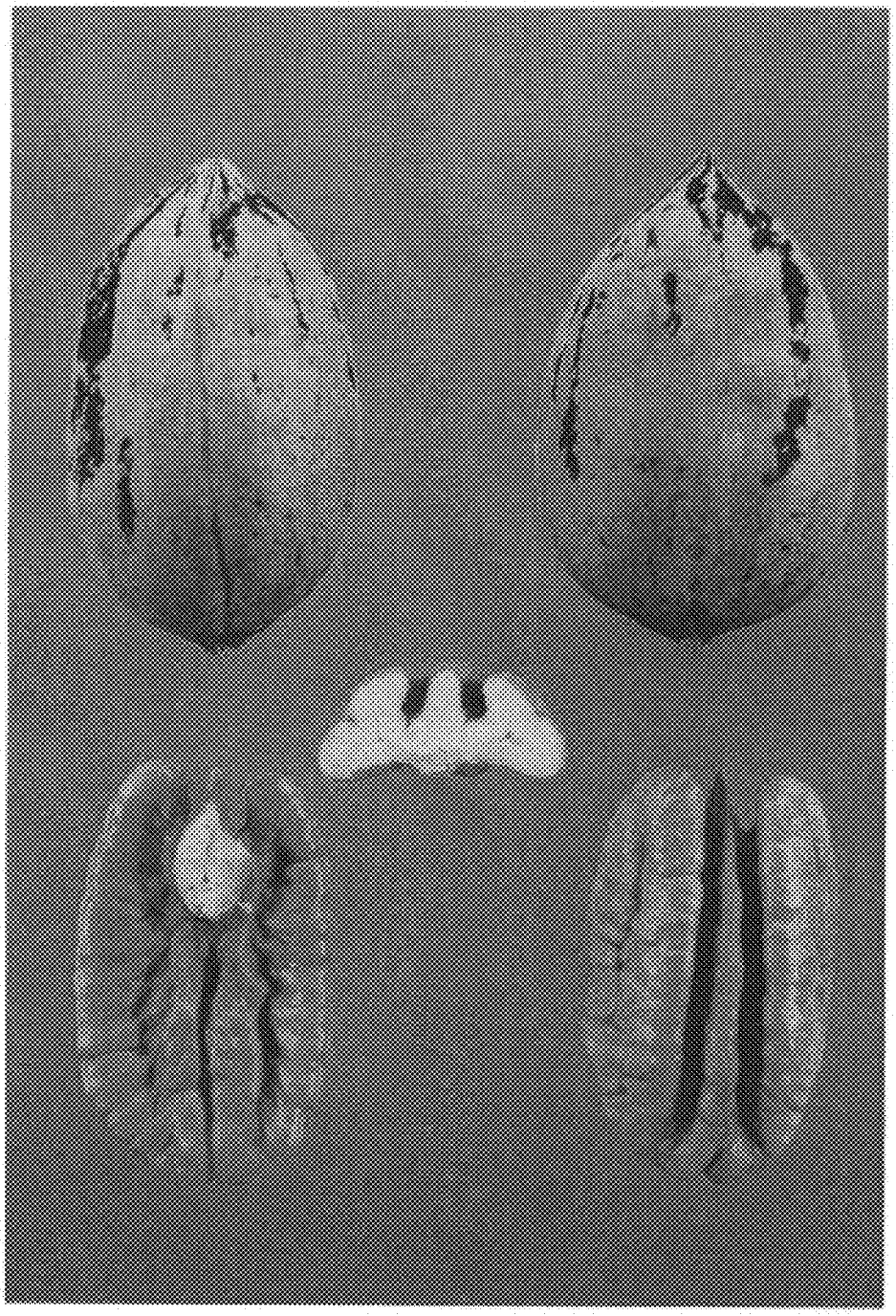
FIG. 7 is a photograph of nut shape and kernel characteristics of 'Whiddon'.

*Sutures*.—Subtle, non-elevated. See the suture side of the nut shown at the upper left-hand position in FIG. 7. The non-suture side is shown at the upper right hand position in FIG. 7.

*Dorsal grooves*.—Wide, thereby decreasing the percentage kernel in the nut. See the kernel section shown in the middle of FIG. 7 and the dorsal side of the kernel shown at the lower right hand position of FIG. 7.

*Ventral grooves*.—Narrow and deep. See the ventral side of the kernel shown at the lower left-hand position of FIG. 7.

*Weight*.—11.3 grams per nut (non-limiting soil moisture).

*Cluster size*.—About 1.8 fruits per mature cluster.

*Texture*.—Faint ridges, slightly rough topography is on non suture surface.

*Shell thickness*.—Moderately thick, 0.78 mm.

*Nut shell color*.—Grey-brown (RHS N199B).

*Kernel color*.—Good color, Grayed-orange (RHS 165B).

*Kernel coat*.—No speckling has been observed.

*Kernel percentage of nut*.—About 56 percent.

*Nut maturity*.—About October 9th. Later than 'Byrd' (U.S. Plant Pat. No. 20,867) by about 15 days.

*Harvestability*.—Exceptionally suitable for machine harvest. Uniform maturity.

*Cracking/shelling ability*.—Cracks exceptionally well, percentage of kernels with intact halves is high. Typically, less than one percent of chipped or broken kernels were observed.

COMPARISONS TO OTHER VARIETIES

Tree form of 'Whiddon' is unusually upright in contrast to both parents and almost all other pecan cultivars. Thus, 'Whiddon' trees can be planted in higher tree density than most cultivars. The timing of bud break of 'Whiddon' is similar to 'Huffman' (U.S. Plant Pat. No. 25,465), 'Morrill' (U.S. Plant Pat. No. 23,335), and 'Stuart' (unpatented) pecan trees (Table 2). Thus, 'Whiddon' is less susceptible to late-spring freezes than 'Byrd' (U.S. Plant Pat. No. 20,867), 'Cunard' (U.S. Plant Pat. No. 24,373), 'Desirable', and 'Treadwell' (U.S. Plant Pat. No. 25,740). The leaves of 'Whiddon' are forest green as in 'Pawnee', but are unlike the pale green of 'Desirable'. Leaflet orientation is similar to seed parent 'Desirable' and most pecan genotypes; that is leaflets droop from the rachis and is unlike pollen parent 'Pawnee' where the opposite leaflets are oriented at 180 degrees relative to each other. Leaflet margins on vigorous shoots are convoluted. The stigmatic surface of 'Whiddon' is oxblood, similar to the oxblood color of both parents and in contrast to the green stigma of 'Wichita' (unpatented) and some other cultivars. 'Whiddon' like 'Tom' (U.S. Plant Pat. No. 26,705) is highly resistant to the scab fungus (Table 3) and contrasts with the high susceptibility of both parents and to almost all other pecan cultivars. In the humid southeastern United States, resistance is a major attribute of 'Whiddon'. Mature bark is pecked by yellow bellied sapsucker as in 'Stuart' and 'Wichita'.

Table 1 below compares periods of pollen shedding and stigma receptively for 'Whiddon' and selected other pecan cultivars (all unpatented) in April 2012, Watkinsville, Ga.

TABLE 1

| | April | | | | | | | | | | | | | | | | | | | | |
|---|---|---|---|---|---|---|---|---|---|---|---|---|---|---|---|---|---|---|---|---|---|
| | 9 | 10 | 11 | 12 | 13 | 14 | 15 | 16 | 17 | 18 | 19 | 20 | 21 | 22 | 23 | 24 | 25 | 26 | 27 | 28 | 29 |
| | 30 | | | | | | | | | | | | | | | | | | | | |
| Protandrous cultivars | | | | | | | | | | | | | | | | | | | | | |
| 'Cheyenne' * | | | | | | | . . . . . | | | | | | | | | | | | | | |
| 'Desirable' * | ____ | ____ | ____ | ____ | | | | | | | | | | . . . . . | | | | | | | |
| 'Whiddon' | | ____ | | | | | | | | | | | | | | . . . . . | | | | | |
| Protogynous | | | ____ | ____ | ____ | ____ | | | | | | | | | | | | | | | |
| 'Elliott' * | | | | . . . . . | | | | | | | | | ____ | ____ | ____ | | | | | | |
| 'Schley' * | | | | | . . . . . | | | | | | | | | | | | | | | | |
| 'Stuart' * | | | | | | | | | . . . . . | | | | | | | | | | | | |

. . . . . = Period of stigma receptivity.
_____ = Period of pollen shedding
* Unpatented Table 2 below compares bud break date for 'Byrd', 'Tom', 'Huffman', 'Morrill', 'Cunard', 'Treadwell', 'Stuart', 'Whiddon', and 'Desirable' pecans. Observations were of trees growing in Watkinsville, Ga.

TABLE 2

| Cultivar | Bud break date[z] |
|---|---|
| 'Byrd' | 3/27c |
| 'Tom' | 4/2a |
| 'Huffman' | 3/30b |
| 'Morrill' | 3/30b |
| 'Cunard' | 3/26c |
| 'Treadwell' | 3/27c |
| 'Stuart' | 3/31ab |

TABLE 2-continued

| Cultivar | Bud break date[z] |
|---|---|
| 'Whiddon' | 3/30b |
| 'Desirable' | 3/27c |

Means followed by the same letter are not statistically different, P ≤ 0.05, n = 6.
[z]Average of years 2005, 08, 09, 10, 11, 12. Replication over years.

Table 3 below compares fruit scab susceptibility of 'Whiddon' with 'Byrd,' 'Morrill,' 'Cunard', 'Treadwell', 'Tom', 'Huffman' and 'Desirable'. In addition, 'Pawnee' has been observed to be more susceptible to scab disease than 'Whiddon' when observed at two Georgia growing locations.

TABLE 3

| | Fruit scab[x] | | | | |
|---|---|---|---|---|---|
| | Leary[y] | | | | Watkinsville[z] |
| Cultivar | 2010 | 2011 | 2012 | 2013 | 5 yr. mean[y] |
| 'Byrd' | 1.1c | 1.0b | 1.0b | 1.0b | 1.7bc |
| 'Morrill' | — | 1.0b | 1.0b | 1.0b | 1.8b |
| 'Cunard' | 1.6b | 1.0b | 1.0b | 1.0b | 2.3b |
| 'Treadwell' | 1.0c | 1.0b | 1.0b | 1.0b | 2.2b |
| 'Tom' | — | 1.0b | 1.0b | 1.0b | 1.0c |
| 'Huffman' | 1.0c | 1.0b | 1.0b | 1.0b | 1.0c |
| 'Whiddon' | 1.0c | 1.0b | 1.0b | 1.0b | 1.0c |
| 'Desirable' | 3.2a | 1.4a | 4.3a | 2.8a | 3.3a |

Means followed by the same letter are not statistically different, P ≤ 0.05.
[x]1 = no lesions, 2 = occasional lesions, <10% of fruit with scab, 3 = lesions common on fruit but not damaging, 1-50% of fruit with scab, 4 = wide spread lesions on fruit but not damaging, 51-75% of fruit with scab, 5 = widespread lesions on fruit, fruit size suppressed. Fungicides applied at both locations.
[y]n = 19, sprayed with fungicide.
[z]n = 5, sprayed with fungicide.

Table 4 below compares nut characteristics of 'Treadwell', 'Byrd', 'Tom', 'Cunard', 'Morrill', 'Elliott', 'Huffman', 'Whiddon', and 'Desirable' pecans. Observations were of trees growing in Albany, Ga., from 2009-2012.

TABLE 4

| Cultivar | Wt./nut (g) | Nuts/lbs (no.) | Nut length (mm) | Length/ width [z] | Nut [y] flatness | Shell thickness (mm) | Kernel (%) | Nut maturity date [x] |
|---|---|---|---|---|---|---|---|---|
| 'Treadwell' | 9.5ef | 48cd | 41.5e | 1.92b | 0.97d | 0.70cd | 62.2b | 24a |
| 'Byrd' | 8.9f | 51c | 42.4e | 1.88bc | 1.04b | 0.51e | 62.3b | 24a |
| 'Tom' | 7.8g | 58b | 36.3f | 1.64e | 0.96d | 0.84a | 54.7d | 25a |
| 'Cunard' | 11.1cb | 41e | 52.2a | 2.18a | 1.03b | 0.66cd | 62.5b | 26a |
| 'Morrill' | 10.1de | 46d | 49.2b | 2.07a | 1.11a. | 0.63d | 65.9a | 35b |
| 'Elliott' | 7.1h | 64a | 32.5g | 1.39f | 1.04b | 0.70cd | 52.0e | 38b |
| 'Huffman' | 12.2a | 37e | 44.7d | 1.65e | 1.03b | 0.72c | 55.5c | 33b |
| 'Whiddon' | 11.3b | 41e | 45.2cd | 1.81bcd | 1.01c | 0.78b | 55.9c | 39b |
| 'Desirable' | 10.4cd | 44d | 46.7c | 1.76cde | 1.11a | 0.72c | 54.8d | 50c |

Means followed by the same letter are not statistically different, P < 0.05, n = 4.
[z] Length to width ratio = nut length divided by width. Width was measured midway the length of the nut and across the suture.
[y] Nut flatness = ratio of nut width across suture to width between suture. Measurement was made midway the length of the nut.
[x] Date when shuck dehiscence had occurred on 50% of the fruit, from September 1.

Pecan nuts of large size that mature relatively early command a premium price. The price per pound normally declines as the harvest becomes later. Consequently, cultivars that exhibit early maturity at harvest are commercially important. The color of a kernel's seed coat (lighter is preferred), and the percentage kernel of the nut also affects the selling price of pecans. Although the nut maturity of 'Whiddon' is about 15 days later than nut maturity of 'Byrd', it is about 11 days earlier than 'Desirable' (Table 4). 'Desirable' is believed to be the leading cultivar now being planted in new orchards in Georgia. Even though the nut maturity of 'Whiddon' is later than 'Byrd', the maturity date is still early enough to be considered an early market cultivar. The later harvest date of 'Whiddon' is advantageous in one respect because a number of growers of pecans in southwest Georgia also grow peanuts. The harvest date of 'Byrd' 'Cunard', 'Pawnee', 'Tom', and 'Treadwell' pecans conflicts with the peanut harvest date. 'Whiddon' matures at the end of the peanut harvesting season, making it a more suitable early cultivar for peanut growers that can harvest 'Whiddon' pecans following the peanut harvest. In addition to use in a new planting, 'Whiddon' is well suited as a replacement tree or as an inter plant in a 'Stuart'-'Schley' (unpatented), 'Desirable' orchard, a common combination in the southeastern United States. The nut maturity date of 'Whiddon' is similar to 'Stuart' and 'Schley'; allowing a once over harvest of the blended nuts. In contrast to 'Treadwell', and similar to 'Tom', the shuck opens widely which minimizes premature germination and promotes rapid pre harvest drying of the nut. Unlike 'Huffman' and 'Treadwell', shuck surface is not russet. Also unlike 'Huffman', shuck sutures of 'Whiddon' are not serrated.

Figure 8A:
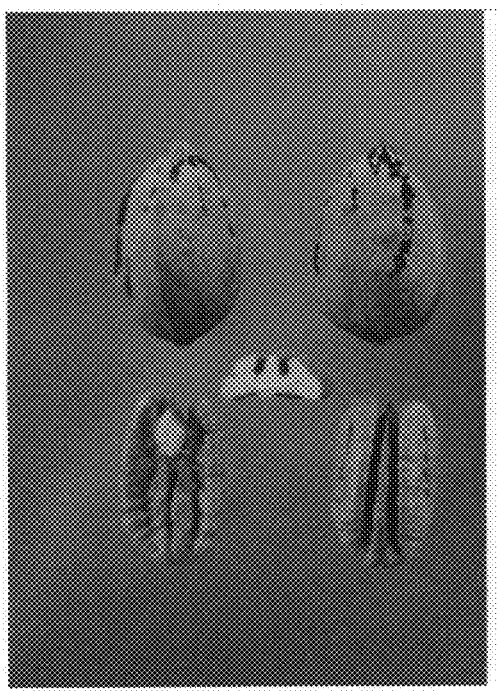
FIGS. 8A and 8B are comparison photographs of nut shape and kernel characteristics of 'Whiddon' vs. 'Desirable'. The 'Whiddon' nuts and kernels are shown in FIG. 8A and the prior art 'Desirable' nuts and kernels are shown in FIG. 8B.
Figure 8B:
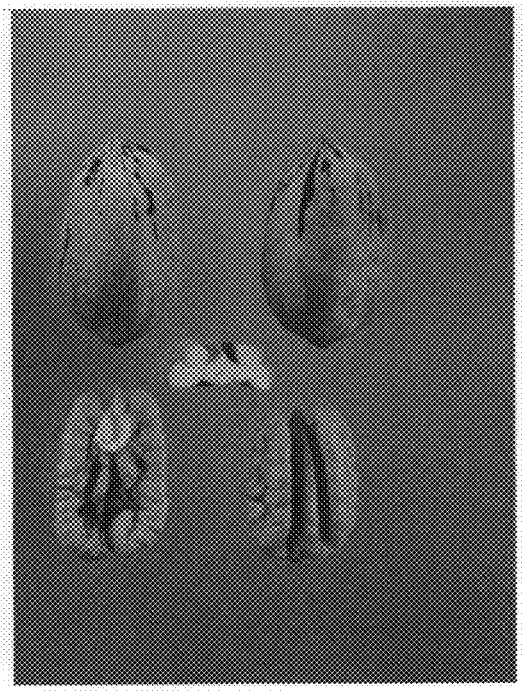
FIG 8B PRIOR ART

From Table 4, 'Whiddon' nuts are large (wt./nut), equal in size to 'Cunard' and larger than 'Morrill' and 'Desirable' and less than 'Huffman'. Consequently, the large kernels of 'Whiddon' are well suited to the "mammoth half" market. Nut length is less than 'Cunard' and 'Morrill' and similar to 'Desirable' and 'Huffman'. General nut shape (length/width) is similar to 'Desirable', 'Treadwell', and 'Byrd', but is less oblong than 'Cunard' and 'Morrill'. Cross-section (nut flatness) of 'Whiddon' nuts are near round (flatness ratio 1.01) and intermediate to 'Huffman' and 'Desirable' and more symmetrical than 'Treadwell', 'Byrd', 'Tom', 'Cunard', 'Morrill', 'Elliott', 'Huffman', and 'Desirable'. The shell is thicker in 'Whiddon' than 'Huffman' and 'Desirable'. The percentage kernel of 'Whiddon' is higher than 'Desirable' and similar to 'Huffman'. In pecans, the percentage kernel is a direct function of shell thickness and the percentage of the shell cavity filled with kernel. The percentage kernel of 'Huffman' and 'Desirable', in spite of a thinner shell, is not greater than 'Whiddon'; because of a concave kernel, dorsal grooves that are wide, and a central partition that is thick, which reduces the percentage of shell cavity filled with kernel. The percentage kernel of 'Whiddon' nuts is higher than the industry standard 'Desirable'. FIGS. 8A and 8B show a comparison of typical nuts and kernels of 'Whiddon' and 'Desirable'. In FIG. 8A, left to right, the suture side and non-suture side of the 'Whiddon' nuts are shown. This FIG. also shows a cross-section of the kernel in the middle and, left to right, the ventral side and dorsal side of the 'Whiddon' kernels. FIG. 8B, left to right, the suture side and non-suture side of the 'Desirable' nut, a cross-section of the 'Desirable' kernel is shown in the middle; and, left to right, ventral and dorsal sides of the 'desirable' kernel are also shown.

Under stress, primarily fruiting stress, and when 'Pawnee' pecan trees are grown in humid southeastern United States, the kernel's seed coat of 'Pawnee' pecans can develop conspicuous and unattractive dark spots. This speckling reduces the marketability of these nuts. Speckling has not been observed to be a problem of 'Whiddon' nuts grown in Georgia. Kernel color of 'Whiddon' fruit is good (FIGS. 7 and 8) and kernel color retention is good. In addition, unlike 'Whiddon', during a heavy "on" nut production year for 'Pawnee' trees growing in Georgia, kernel development is relatively poor, resulting in a high percentage of the nuts being unmarketable or of reduced value.

Table 5 below compares precocity of 'Cunard', 'Byrd', 'Treadwell', 'Tom', 'Desirable', 'Morrill', 'Whiddon', 'Elliott', 'Huffman', and 'Stuart' pecans.

TABLE 5

| Cultivar | Years to initial fruiting[z] |
|---|---|
| 'Cunard' | 2 |
| 'Byrd' | 3 |
| 'Treadwell' | 3 |
| 'Tom' | 3 |
| 'Desirable' | 4 |
| 'Morrill' | 4 |
| 'Whiddon' | 4 |
| 'Elliott' | 5 |
| 'Huffman' | 5 |
| 'Stuart' | 6 |

[z]Years from transplanting from the nursery.

Table 6 below compares alternate bearing tendency of 'Byrd', 'Treadwell', 'Huffman', 'Tom', 'Cunard', 'Morrill', and 'Whiddon' pecans. Observations were of trees growing in Albany, Ga.

TABLE 6

| Cultivar | Years to fruiting (no.) | Years until bearing alternate (no.)[y] |
|---|---|---|
| Byrd | 2 | 3 |
| Treadwell | 2 | 3 |
| Huffman | 2 | >6 |
| Tom | 2 | >6 |
| Cunard | 2 | 10[z] |
| Morrill | 2 | >9 |
| Whiddon | 2 | 8 |

[y]Years after top working mature trees to the respective cultivar.

Top working simulates a mature tree and allows for earlier evaluation of alternate bearing, kernel development under heavy fruit load, and suitability for mechanical harvest and ease of fruit thinning.

[z]Annual production maintained by fruit thinning.

Table 7 below compares pounds/tree, weight per nut, nuts per pound, percentage kernel of trees top worked[z], namely the comparison is of 'Morrill', 'Cunard', 'Treadwell', 'Huffman', 'Tom', and 'Whiddon' pecans, observed in Albany, Ga., from 2009-2012.

TABLE 7

| Cultivar | Lbs/tree | wt./nut (g) | Nuts/lb. (no.) | Kernel (%) |
|---|---|---|---|---|
| 'Morrill' | 35b | 10.1c | 46d | 65.9a0 |
| 'Cunard'[y] | 44ab | 11.1b | 41e | 62.5b |
| 'Treadwell'[y] | 30ab | 9.5cd | 48cd | 62.2b |
| 'Huffman' | 32ab | 12.2a | 37e | 55.5cd |
| 'Tom' | 57a | 7.8e | 58b | 54.7cd |
| 'Whiddon' | 37ab | 11.3b | 41e | 55.9c |

Means followed by the same letter within a column are not statistically different, $P \leq 0.05$, $n = 4$.

[z]Top working simulates a mature tree and allows for earlier evaluation of alternate bearing, kernel development under heavy fruit load, and suitability for mechanical harvest and ease of fruit thinning

[y]Cunard and Treadwell were fruit thinned as needed. About 50% of the fruit was removed. Other cultivars were not fruit thinned.

'Whiddon' is not precocious relative to 'Byrd' (Table 5). Also, the original 'Whiddon' tree bore its first fruit the 13$^{th}$ year from planting as seed. In comparison, the original tree of 'Byrd' first fruited the 7$^{th}$ year from planting as seed. 'Whiddon' is not as precocious as 'Byrd' as is also indicated by the onset of alternate fruit-bearing in 'Byrd' trees the third year from top working in contrast to alternate fruit bearing in 'Whiddon' trees in the 8$^{th}$ year (Table 6). Precocity of 'Whiddon' is similar to 'Desirable' and 'Morrill' (Table 5). Although not precocious, prolificacy as mature top worked trees is good and similar to 'Morrill', 'Cunard', 'Treadwell', 'Huffman', and 'Tom' (Table 7). Thus far, alternate bearing of 'Whiddon' has been relatively minor or about 50% during the "off" year relative to the "on" year. Thus, the mainly annual production of 'Whiddon' is as in 'Desirable' and both 'Whiddon' and 'Desirable' have a small fruit cluster size (Table 8).

As indicated in (Table 8), the cluster size of 'Whiddon' and 'Desirable' is similar. It does appear that 'Whiddon' has lower density of fruiting shoots than 'Byrd' and is similar to 'Desirable'. Because of the small cluster size and consistent production exhibited by 'Whiddon' following top working to mature pecan trees, 'Whiddon' is expected to bear quite consistently with increasing tree maturity as occurs with its seed parent 'Desirable'. 'Whiddon' is superior to 'Desirable' in having a larger nut, higher percentage kernel, and high resistance to scab disease.

Table 8 below compares fruit cluster size of 'Byrd', 'Desirable', 'Huffman', 'Tom', 'Morrill', 'Pawnee', Cunard', and 'Treadwell', 'Elliott', and 'Whiddon' pecans. Observations were of trees growing in Watkinsville, Ga. Data are averages of three years, 2005, 2006, and 2008.

TABLE 8

| Cultivar | Fruits/cluster(no.)[z] |
|---|---|
| 'Byrd' | 3.1a |
| 'Desirable' | 1.8c |
| 'Huffman' | 1.6c |
| 'Tom' | 2.8b |
| 'Morrill' | 2.9ab |
| 'Pawnee' | 3.2a |
| 'Cunard' | 3.2a |
| 'Treadwell' | 2.7b |
| 'Elliott' | 2.8b |
| 'Whiddon' | 1.8c |

Means followed by the same letter are not statistically different, $P \leq 0.05$, $n = 30$.

[z]Cluster counts made after the second drop was completed.

Tables 9-11 below compares N scorch, black pecan aphids, and pecan leaf scorch mite resistance of 'Whiddon' to other pecan varieties.

Table 9 below compares leaf susceptibility of 'Byrd', 'Morrill', 'Cunard', 'Treadwell', 'Whiddon', 'Huffman', and 'Desirable' pecans to N scorch[y]. Observations were of trees growing in Leary, Ga. in 2009.

TABLE 9

| Cultivar | Leaf rating[z] |
|---|---|
| 'Byrd' | 1.2c |
| 'Morrill' | 1.5c |
| 'Cunard' | 1.1c |
| 'Treadwell' | 1.0c |
| 'Whiddon' | 1.1c |
| 'Huffman' | 3.8b |
| 'Desirable' | 4.7a |

Means followed by the same letter are not statistically different, P ≤ 0.05%, n = 19.

[y]N scorch can cause severe premature defoliation in May and July and is induced by an imbalance of N and K in the leaf.

[z]1 = no scorch

2 = <1% of leaves with scorch

3 = 2 to 20%

4 = 21 to 40%

5 = >41%

Table 10 below compares leaf susceptibility of 'Byrd', 'Huffman', 'Morrill', 'Cunard', 'Tom', 'Treadwell', 'Sumner', 'Whiddon', and 'Desirable' to black pecan aphid. Observations were of trees growing in Leary, Ga.

TABLE 10

| | Leaf rating[z] | | |
|---|---|---|---|
| | Year | | |
| Cultivar | (2009) | (2010) | (2011) |
| 'Byrd' | 1.5ef | 1.7cd | 1.7bc |
| 'Huffman' | 1.4efg | — | 1.4cd |
| 'Morrill' | 2.3b | 2.0ab | 1.9b |
| 'Cunard' | 1.1g | 1.9abc | 1.8b |
| 'Tom' | 1.1g | — | 1.2de |
| 'Treadwell' | 1.9cd | 2.2a | 2.4a |
| 'Sumner' | 2.8a | — | 1.9b |
| 'Whiddon' | 1.9c | 2.0ab | 2.0b |
| 'Desirable' | — | 2.0ab | 1.0e |

Means followed by the same letter are not statistically different, P ≤ 0.05%, n = 19.

[z]1 = no injury, 2 = <1% of leaves with injury, 3 = 1-10% of leaves with injury, 4 = 11-50% of leaves with injury, 5 = >50% of leaves with injury and partial defoliation.

Table 11 below compares leaf susceptibility of 'Byrd', 'Tom', 'Morrill', 'Huffman', 'Cunard', 'Treadwell', 'Whiddon', 'Sumner', and 'Desirable' to pecan leaf scorch mite. Observations were of trees growing in Leary, Ga.

TABLE 11

| | Leaf rating[z] | |
|---|---|---|
| Cultivar | 2009 | 2010 |
| 'Byrd' | 1.1f | 1.1c |
| 'Tom' | 1.1f | — |
| 'Morrill' | 1.2f | 1.2c |
| 'Huffman' | 1.6de | — |
| 'Cunard' | 2.2bc | 1.8ab |
| 'Treadwell' | 2.7a | 1.9a |
| 'Whiddon' | 1.6de | 1.6b |
| 'Sumner' | 1.6de | — |
| 'Desirable' | — | 1.0c |

Means followed by the same letter are not statistically different, P ≤ 0.05%, n = 19.

[z]1 = no damage, 2 = trace, 3 = multiple lesions, 4 = minor defoliation, 5 = severe defoliation.

'Whiddon' has excellent resistance to N scorch, in contrast to 'Huffman' and especially to its seed parent 'Desirable' (Table 9). Resistance to black pecan aphid by 'Whiddon' is similar to 'Desirable' (Table 10) and resistance to pecan leaf scorch mite of 'Whiddon' is similar to 'Huffman' (Table 11).

Under the humid growing conditions in southeastern United States, the pecan fruit is highly susceptible to splitting during the "water stage" (liquid endosperm stage) of fruit development. Fruit split can occur following rain and accompanying prolonged high humidity in early August in Georgia. Water split has not been observed in 'Whiddon'. The lack of split may be due to the timing of fruit development. Water split is most likely to occur on cultivars when the maximum liquid endosperm stage occurs during the first two weeks in August; which often coincides with the rainy period in Georgia. Typically, rainfall in Georgia sharply decreases after August 15th. The maximum liquid endosperm stage in 'Whiddon' fruit grown in Georgia usually occurs after August 15th.

The 'Whiddon' pecan tree is therefore an improved new and distinct pecan.

I claim:

1. A new and distinct cultivar of pecan tree, as herein illustrated and described.

* * * * *